United States Patent
Sandler

[11] B 3,981,785
[45] Sept. 21, 1976

[54] ELECTROCHEMICAL SENSOR FOR REACTIVE GAS MIXTURES

[75] Inventor: Yehuda L. Sandler, Pittsburgh, Pa.

[73] Assignee: Westinghouse Electric Corporation, Pittsburgh, Pa.

[22] Filed: July 18, 1969

[21] Appl. No.: 843,038

[44] Published under the second Trial Voluntary Protest Program on February 3, 1976 as document No. B 843,038.

[52] U.S. Cl. .............................. 204/195 S; 204/1 T
[51] Int. Cl. ........................................... G01n 27/46
[58] Field of Search ............ 136/86 F; 204/1 T, 195

[56] References Cited
UNITED STATES PATENTS

| | | | |
|---|---|---|---|
| 3,216,911 | 11/1965 | Kronenberg | 204/195 |
| 3,347,767 | 10/1967 | Hickam | 204/195 |
| 3,400,054 | 9/1968 | Ruka et al. | 204/195 S |
| 3,481,855 | 12/1969 | Kolodney et al. | 204/195 |
| 3,514,377 | 5/1970 | Spacil et al. | 204/1 T |
| 3,597,345 | 8/1971 | Hickam et al. | 204/195 S |

Primary Examiner—T. Tung
Attorney, Agent, or Firm—M. P. Lynch

[57] ABSTRACT

An electrochemical device is designed to respond to a constituent such as oxygen in a reactive mixture which may include a fuel such as methane. The device includes an electrochemical cell employing an electrolye such as a stabilized zirconia associated with two electrodes and designed for operation at an elevated temperature such as 200°C to 1000°C. An electrode for such a cell is designed to have no catalytic action on the mixture.

The system may be arrnaged to assure a full reaction of the mixture before the cell responds to the desired constituent. Thus the mixture may also be subjected to the action of a catalyst before it reaches the electrode area. If the mixture is applied to another non-catalytic cell before it is subjected to the catalyst further information is obtained concerning the desired constituent. The amount of a constituent such as oxygen present before and after the mixture is catalyzed may be compared to provide an indication of the amount of another constituent of the mixture such as methane.

8 Claims, 7 Drawing Figures

INVENTOR
Yehuda L. Sandler

ELECTROCHEMICAL SENSOR FOR REACTIVE GAS MIXTURES

BACKGROUND OF THE INVENTION

1. Field of the Invention:

This invention relates to electrochemical cells and it has particular relation to electrochemical cells which are responsive to a constituent of a reactive mixture.

The invention is particularly desirable for developing information from a solid electrolyte cell concerning oxygen present in a chemically reactive combustible mixture which may include a fuel such as methane. For this reason the invention will be described as applied to oxygen-responsive devices.

2. Description of the Prior Art:

Galvanic cells for measuring the oxygen content of gasses are well known. For example, cells using a hydroxide-ion conducting electrolyte, that consists of a fused alkali hydroxide or aqueous hydroxide, can be used to obtain an electric output responding to differences in oxygen concentration at two electrodes in the same electrolyte.

A particularly useful device utilizes the oxygen ion conductivity of certain solid oxides. Such solid electrolytes may consist of an oxide of a tetravalent element such as zirconium, thorium, or hafnium suitably doped with an oxide of elements of lower valency to impart a greater ionic conductivity to the tetravalent oxides. Reference is made to a patent of R. J. Ruka and J. Weissbart, U.S. Pat. No. 3,400,054. The electrolyte is bounded by two electronically conducting electrodes. The cathode, the positive pole of the cell, is in contact with the higher oxygen concentration. The reaction here is

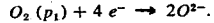

At the anode

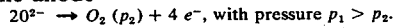

The voltage E at open circuit, or when small enough currents are drawn from the cell, is given by the Nernst equation $$E = 4.954 \times 10^{-5} T \log p_1/p_2$$

where T is the temperature on the absolute scale. $P_1$ may be the reference pressure. For example, it can be supplied by air at atmospheric pressure or by the vapor pressure of an oxide applied to the electrode.

As described in the Hickam U.S. Pat. No. 3,347,767 such a cell may comprise a tubular electrolyte member of a solid material such as a calcium-stabilized zirconium-oxide electrolyte. Such a member may have a length of eight inches an inner diameter of ⅛ inch and an outer diameter of 3/16 inch. The tube is coated with inner and outer porous electrodes of platinum. When operated at a suitable temperature such as 400°C to 1000°C (850°C is very satisfactory) such a cell develops an electrical output from the electrodes which is dependent on the ratio of the partial pressures of oxygen present at the two electrodes. Reference may also be made to the Hickam U.S. Pat. No. 3,404,836.

SUMMARY OF THE INVENTION

An oxygen gauge of the type described can be used with gas mixtures containing oxygen, even in the presence of an oxidizable gas. When the temperature of operation of the cell is chosen high enough, usually above 800°C, and the electrode in contact with the active mixture is in a catalytically active state, complete equilibrium will be established and the gauge will then indicate the equilibrium partial pressure of oxygen. If there is an excess of oxygen in the mixture entering the cell, the gauge will give an indication of the excess oxygen over stoichiometric requirements for complete oxidation. When the cell is, for example, connected to the stack of a furnace, the voltage signal obtained from the cell also gives the excess oxygen concentration for the gas-air mixture entering the furnace.

I have found that if the mixture reaching the electrodes is incompletely reacted erroneous results may be obtained. Surprisingly, the output voltages can be so high that the gauge reading can be erroneously interpreted as showing an excess of fuel in spite of the actual presence of an excess of oxygen. The reason for this behavior presumably is the catalytic production of hydrogen in the non-equilibrium mixture. Due to its high diffusion rate to the electrode-electrolyte interface and its high electrochemical activity, the hydrogen has an effect on the voltage out of proportion to its actual concentration. The electrodes heretofore employed do not assure complete reaction of the mixture.

In accordance with the invention a catalyst is located in the path of the mixtures applied to an oxygen sensor for the purpose of assuring complete reaction of the constituents of the mixture. This assures accurate results from the sensor.

Preferably the catalyst is located in the heated tube with which the electrodes are associated. A separate source of heat for the catalyst is thus unnecessary. A device employing a catalyst in this way may be termed an "equilibrium" device.

According to another aspect of the invention, a gauge is constructed in such a manner that the composition of the reactive mixture is unaffected by the electrodes and the cell indicates the true oxygen partial pressure in the mixture. Such a device may be termed a "non-equilibrium" device. If the device is preceded by a separate catalyst the combination becomes an "equilibrium" device.

The invention also contemplates the combination of the equilibrium and non-equilibrium devices for the measurement of combustible fuels as well as the oxygen in a mixture. Thus it may control the composition of various mixtures such as furnace gases, and exhausts of internal-combustion engines and anti-air-pollution devices. While the non-equilibrium part determines the actual partial pressure of the oxygen in the mixture entering the gauges the equilibrium part determines the excess partial pressure after completion of the reaction. The two readings indicate the amount of oxygen consumed by the fuel entering the first gauge and therefore indicates the oxygen equivalent of the fuel.

The use of a separate catalyst facilitates the adoption of electrodes of the same material throughout, thus avoiding contact potential differences, when precision is of importance.

One form of the invention is particularly suited when no reference gas such as pure air or oxygen is available. Provision is made for equilibrating a portion of the mixture and supplying such portion to the interior of an electrolyte tube. Alternately a catalytically active electrode is used. The other portion of the mixture which is not equilibrated is applied to the exterior of a tube. The voltage appearing across the electrodes is due to the different oxygen contents of the equilibrated and not-equilibrated gas mixtures at the two electrodes. No separate catalyst may be required in the equilibrium part of the combined system of equilibrium and non-equilibrium gauge if a good catalytic material is used under suitable conditions. There are several factors which aid in controlling the activity. Thus, the porosity of the electrode material, the size of the electrodes, the flow rate of the gas, the temperature of operation all affect to a certain extent the degree of reaction in the mixture. In the equilibrium gauge a large surface area (determined for example by porosity and size of the electrode), a low flow rate, and a high temperature of operation, usually above 800°C, will all aid to assure equilibration of the mixture. In the non-equilibrium gauge the electrode material is chosen so as to provide little or no activity. A low surface area of the electrode, a high flow rate and a low temperature of operation aid in avoiding the reaction of the fuel with the oxygen. The temperature chosen for the non-equilibrium gauge can only be chosen so low as consistent with the lower current that can be drawn from the device without loss in output voltage due to electrode polarization and voltage drop over the electrolyte. (The latter can be kept lower by choice of a thin electrolyte). Availability of only a small current would necessitate the use of a relatively expensive voltmeter of high impedance.

It was found that certain materials, above all silver, make it possible to operate the non-equilibrium gauge at a relatively high temperature, up to about 850°C, without the use of unduly high flow rates and still obtain correct readings of the true oxygen partial pressure in the mixture. This makes it possible to use an inexpensive meter and, if desired, to run the combination of equilibrium gauge and non-equilibrium gauge at the same temperature and flow rate.

It is therefore an object of the invention to provide a solid-electrolyte electrochemical cell having an electrode which does not affect the mixture supplied to the cell.

It is another object of the invention to provide a device including a solid-electrolyte electrochemical cell wherein a mixture supplied to the cell is fully reacted prior to application to the cell.

It is also an object of the invention to provide a solid-electrolyte electrochemical device for determining the actual partial pressure of a constituent of a mixture having reactive components and the excess partial pressure of such constituent after the completion of the reaction of the constituents of the mixture.

It is an additional object of the invention to provide a solid-electrolyte electrochemical device for measuring the concentration of a gas of low reactivity in a mixture.

It is a still further object of the invention to provide an improved method of operating a solid-electrolyte electrochemical device.

Other objects of the invention will be apparent from the following description taken in conjunction with the accompanying drawing in which.

DESCRIPTION OF PREFERRED EMBODIMENTS

Figure 1:
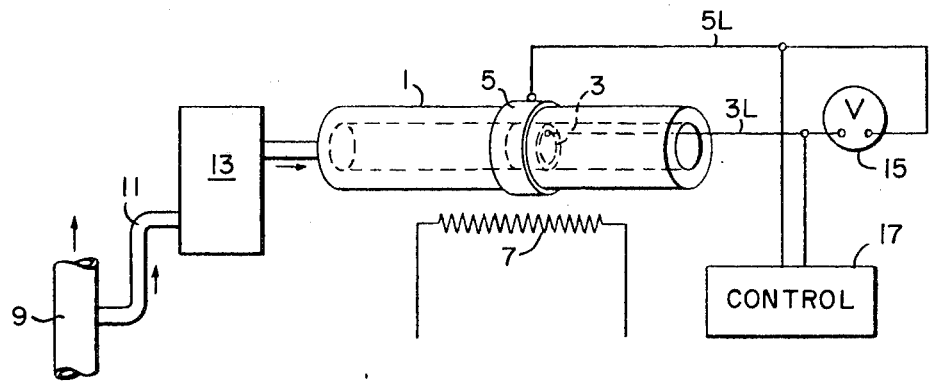
FIG. 1 is a view with parts shown in perspective and parts shown schematically of an oxygen-responsive device embodying the invention.

Referring to the drawing FIG. 1 shows a solid-electrolyte electrochemical device which is capable of measuring a constituent of a fluid mixture which has reactive components. The device is suitable for measuring the oxygen content of a gas mixture in the presence of a combustible gas.

The device employs an electrochemical cell having a solid electrolyte which may be similar to the electrolyte described in the aforesaid Hickam U.S. Pat. No. 3,347,767. In one embodiment of the invention the electrolyte is in the form of a tube which is a solid solution of zirconium oxide and calcium oxide as described in such Hickam patent. Thus the tube may have an inner diameter of 1/8 inch, an outer diameter 3/16 inch and a length of 8 inches.

In the Hickam patent the electrolyte tube is provided with a pair of large-area platinum electrodes. In the presence of an oxidizable gas the platinum electrode usually catalyzes the combustion of the fuel, at least in part, and the device therefore will not respond to the true oxygen partial pressure of the gas mixture entering the cell.

In accordance with one aspect of the present invention an electrode is employed which does not force a reaction between the constituents of the mixture supplied to the cell. Thus it does not catalyze the oxidation of an oxidizable gas in the mixture, and the device may be termed a non-equilibrium device.

As shown in FIG. 1 the tube 1 is provided with an inner electrode 3 and an outer electrode 5. The inner electrode is constructed of a material which is a poor catalyst for the oxidation of the fuel.

The electrodes must be chemically inert to the electrolyte, particularly when a liquid or semi-solid electrolyte is chosen. Furthermore, the electrode material should be a catalyst as poor as possible for equilibrating the mixture while proving a good electrode for the constituents to be measured, e.g., oxygen in our example.

Silver is an excellent example of such electrode material when the fuel is a saturated hydrocarbon like methane. Preferably the outer electrode 5 is constructed of the same material. Other examples of suitable electrode materials are silver-based alloys such as silver-and-gold or silver-and-palladium alloy.

In order to reduce the catalytic effect of the electrode still further it is given a relatively small area. Thus the two electrodes 3 and 5 may have a width of four millimeters. The silver may be applied in the same manner as the platinum discussed in the Hickam U.S. Pat. No. 3,347,767. For present purposes it will be assumed that the electrodes are made from silver paste.

A preferred flow rate for the tube 1 having a diameter of 1/8 inch is approximately 10 to 1000 cubic centimeters per minute and the preferred temperature range of operation is 550°C to 850°C. The desired operating temperature is determined by an electric furnace which is represented by a heating resistor 7.

In FIG. 1 the mixture of gas to be measured is derived from a furnace stack or flue 9. The mixture to be measured is assumed to contain some oxygen and some unreacted combustible gas such as methane. This mixture is drawn from the flue 9 through a duct 11 and is applied through a flow-meter 13 to the tube 1. An electric output may be derived from the electrodes 3 and 5 which is dependent on the oxygen partial pressure of the gas mixture entering the tube. The electric output is applied to a voltmeter 15 which is calibrated to indicate the oxygen concentration of the mixture and the output also may be employed for control purposes of application to a control device 17 which may be similar to that shown in the Hickam U.S. Pat. No. 3,404,836.

The electrodes 3 and 5 may be connected through leads 3L and 5L which are narrow trips or stripes of material similar to that of the electrodes and applied in the same way from the electrodes towards an accessible part of the tube.

To illustrate the operation of the non-equilibrium device by a typical example, tube 1 was operated at a temperature of 794.7°C and the gas mixture at a flow rate of 65 cubic centimeters per minute was supplied to the tube. The reference gas on the outer electrode was air. The gas mixture contained 0.86 mole per cent methane, 88.46% nitrogen, 2.16% oxygen, and 8.52% carbon dioxide, as determined by mass spectrometric analysis. A voltage of 51.8 millivolts was indicated by the voltmeter. This value agrees with the theoretical voltage, as calculated from the Nernst equation, to within 0.3 millivolt. The deviation corresponds to an error of only 0.028 in the given oxygen value.

In another rather striking experiment demonstrating the usefulness of the device, the oxygen in an explosive mixture was measured at 697°C. Again silver electrodes were used. The composition of the gas was 27.0% methane, 58.5% nitrogen, 14.5% oxygen. In spite of a rather low flow rate of 15 cc/minute chosen, no reaction took place in the mixture going through the tube. A voltage output of 7.85 millivolt was measured, as compared to 7.90 millivolt calculated by the Nernst equation from the actual oxygen pressures. In terms of oxygen partial pressures the agreement is better than 0.3%.

In some cases it was desired to monitor the partial pressure of a constituent such as oxygen in a completely reacted mixture of fuel and air. In the presence of an excess of oxygen a measurement in this manner is obtained for the relative oxygen excess over stoichiometric requirements in the unreacted fuel-air mixture. If the mixture is not completely reacted at the electrodes the information derived from the electrodes does not indicate accurately the desired excess. In order to assure correct information of the desired type a catalyst is inserted in the hot section of the electrolyte tube upstream of the electrode.

Figure 2:
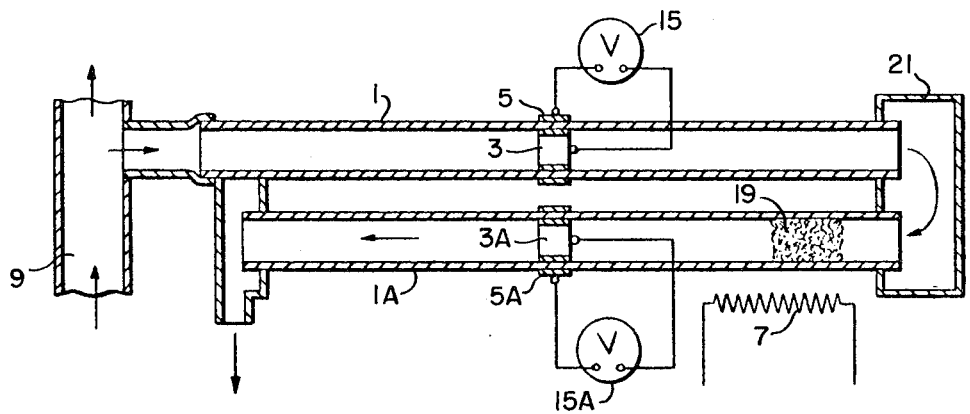
FIG. 2 is a view in cross-section with parts shown schematically of a combined equilibrium and non-equilibrium oxygen-sensitive device embodying the invention.

FIG. 2 shows one way to combine the two types of gauge. A tube 1A, electrodes 3A and 5A and a voltmeter 15A correspond to the elements 1, 3, 5 and 15 of FIG. 1. A catalyst 19 is inserted in the tube 1A upstream of the electrode 3A. The catalyst may be of a conventional type for the desired reaction. Excellent results have been obtained from finely-dispersed platinum. For example, the platinum may be dispersed on asbestos or alumina.

If the gas mixture passes through the tube 1A in the direction of the arrow it first encounters the catalyst 19 and is fully reacted. Consequently the electric output of the electrodes 3A and 5A correctly represents the oxygen excess over stoichiometric requirements. Inasmuch as the mixture at the electrode 3A is fully reacted the device may be referred to as an equilibrium device.

The equilibrium and non-equilibrium devices can also be combined into a single unit. The non-equilibrium device determines the actual partial pressure of the oxygen in the mixture whereas the equilibrium device gives the excess oxygen partial pressure after completion of the combustion and therefore also the oxygen-equivalent of the fuel present. The output of the equilibrium device when connected to the stack of the furnace may also give the excess percentage of oxygen in the fuel-air mixture entering the furnace.

FIG. 2 illustrates a combination of the two devices. It will be noted that in addition to the tubes 1A and its associated components and the tube 1 of FIG. 1 and its associated components are also reproduced. It will be noted that in FIG. 2 the mixture to be measured enters the tube 1 at the left and proceeds through the tube 1 to a connection 21. From the connection 21 the mixture proceeds through the tube 1A. The directions of flow are shown by arrows in FIG. 2. It will be noted that the electric heater as represented by the furnace 7 provides heat for both of the tubes 1 and 1A and for the catalyst 19 within the tube 1A. In a preferred embodiment of the invention, when a high accuracy is desired, all of the electrodes 3, 3A, 5 and 5A are of similar material which is essentially non-catalytic with respect to the mixture being measured. This eliminates the possibility of contact potential differences between dissimilar electrodes.

Electrodes 5 and 5A can be internally connected. The other connections are conveniently made by stripes of the electrode material leading from the electrodes to cold portions of the tubes.

In FIG. 2 the voltmeter 15 measures the actual partial pressure of the oxygen in the mixture which may be derived from a furnace stack. The voltmeter 15A indicates the excess oxygen partial pressure after completion of the combustion and also the oxygen equivalent of the fuel present. The voltmeter 15A thus indicates the excess percentage of oxygen in the fuel-air mixture entering the furnace represented by the stack 9.

Figure 3:
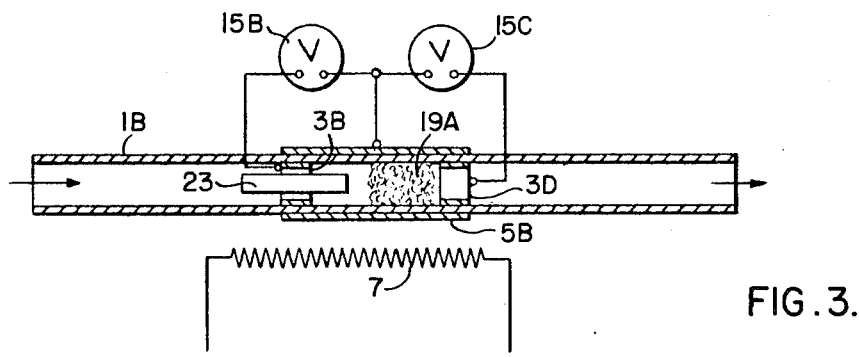
FIG. 3 is a view in cross-section with parts shown schematically of a modified form of a combined equilibrium and non-equilibrium oxygen sensitive device.

The two tube arrangement of FIG. 2 may be replaced by a single tube 1B as shown in FIG. 3. The tube 1B is similar in construction to the tube 1 previously described. The electrodes 3B and 5B correspond to the electrodes 3 and 5 previously described but it will be noted that the electrode 5B has a width greater than that of the electrode 5. The voltmeter 15B corresponds to the voltmeter 15 previously described and measures the non-equilibrium voltage for the mixture entering the tube 1B in the direction of the arrow.

After passing the electrode 3B the mixture being measured passes through a catalyst 19A which corresponds to the catalyst 19 of FIG. 2. The catalyst 19A assures complete reaction of the constituents of the mixture before they reach an electrode 3D. The electric output occurring between the electrode 3D and the electrode 5B is applied to a voltmeter 15C which corresponds to the voltmeter 15A of FIG. 2. The voltmeter 15C thus presents an equilibrium reading for the mixture entering the tube 1B. The electric furnace represented by the electric heater 7 raises the temperature of the tube 1B and the catalyst 19A to the desired operating temperature.

Figure 4:
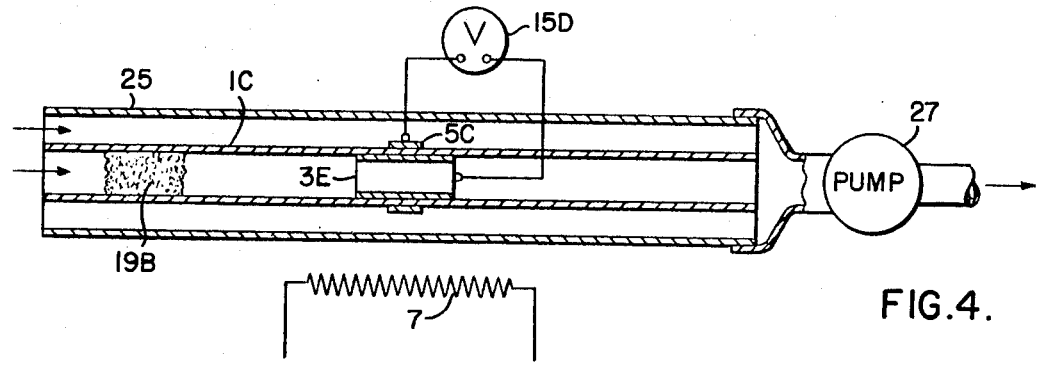
FIG. 4 is a view in cross-section with parts shown schematically of a device requiring no pure reference gas and responsive to the concentration of the reactive fluid such as methane in a mixture containing constituents such as oxygen.

A plug 23 of non-catalytic material such as a alumina is inserted at the electrode 3B to obtain a higher linear velocity of the mixture being measured and thus to reduce back diffusion from the region of the catalyst 19a. In the embodiments of FIGS. 1, 2 and 3 the electrodes 5, 5A and 5B are exposed to the ambient air which provides the reference oxygen. In FIG. 4 the same mixture supplies the environment for each of the electrodes. This is particularly desirable when no uncontaminated air is available to provide the reference oxygen and is therefore useful as a gas detector particularly for mine safety purposes.

In FIG. 4 a tube 1C is disposed which is similar to the tube 1 previously described. The tube has associated therewith an inner electrode 3E, an outer electrode 5C, a voltmeter 15D and a catalyst 19B which corresponds to the components 3, 5, 15 and 19 previously described. In addition a tube 25 of any inert material surrounds the tube 1C for the purpose of providing an annular conduit between the two tubes. A pump 27 provides a small decrease in pressure at the right-hand end of the tubes for the purpose of drawing the mixture to be measured through the tubes in the directions shown by the arrows. It will be noted that the mixture passing through the tube 1C first encounters the catalyst 19B for the purpose of completing the reaction of the constituents of the mixture.

The electrode 5C is a small electrode of a material having a poor catalytic action such as silver, when the fuel consists of saturated hydrocarbons. Preferably the electrode 3E is of similar material to eliminate contact potential problems. The voltmeter 15D measures the electric output between the non-equilibrium electrode 5C and the equilibrium electrode 3E. The electric furnace represented by the electric heater 7 is employed for heating the tubes and catalyst shown in FIG. 4.

To illustrate the operation of the device shown in FIG. 4 it will be assumed that the air in which the device is located contains 1% by volume of methane. The composition of the mixture supplied to the tubes comprises 99 mole per cent of a quantity having 20 parts oxygen and 80 parts nitrogen and comprises 1% of methane. The composition at the electrode 5C then is 1% methane, 19.8% oxygen and 79.2% nitrogen. At the inner electrode 3E, due to complete oxidation of the methane, the composition is 1% carbon dioxide, 2% water, 17.8% oxygen and 79.2% nitrogen. With an operating temperature of 700°C, an output of about 2 millivolts is produced corresponding to an oxygen partial pressure ratio of 17.8 to 19.8.

When the methane concentration reaches 10% by voluem the oxygen inside the tube 1C will be used up and the output voltage rapidly rises with increasing methane concentration to the region of 100 to 1000 millivolts. Thus the presence of a dangerous concentration of methane can be detected.

Figure 5:
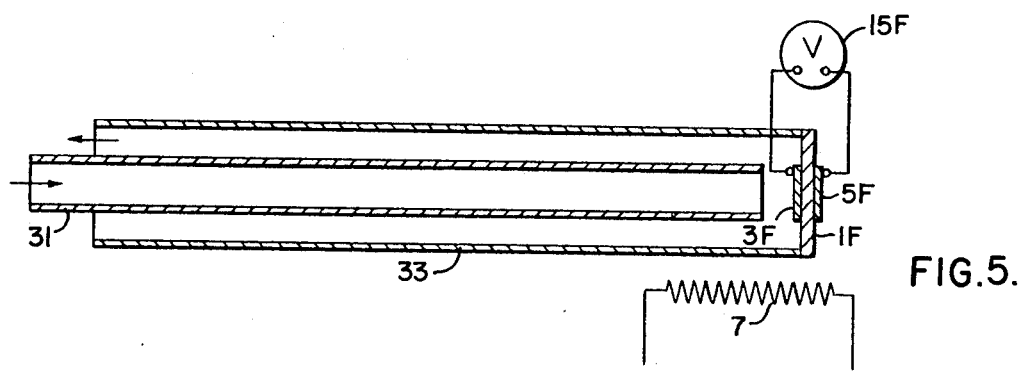
FIGS. 5–7 are views in cross-section with parts shown schematically of further embodiments of the invention.

Other configurations may be employed for the electrolyte. Thus in FIG. 5 the electrolyte is in the form of a disc 1F. This disc has small electrodes 3F and 5F on its two faces corresponding to the electrodes 3 and 5 of FIG. 1 and connected to a voltmeter 15F. The mixture of gas to be measured is directed towards the electrode 3F and the left-hand face of the disc 1F in FIG. 5 through an inner duct 31 and leaves through the space been the inner duct 31 and an outer concentric duct 33.

Figure 6:
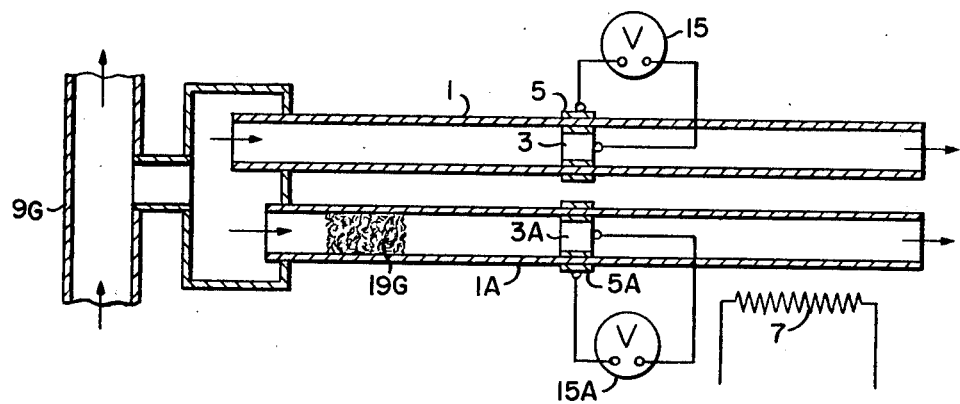

In FIG. 2 the mixture is transmitted through the tubes 1 and 1A in series. If desired the mixture may be transmitted through the tubes in parallel. This is shown in FIG. 6 wherein the mixture is supplied from the stack 9G in parallel through the tubes 1 and 1A. The only other difference between FIGS. 2 and 6 is that the catalyst 19 of FIG. 2 is replaced by a catalyst 19G in FIG. 6 which is located on the left side of the electrode 3A to react the mixture before the mixture reaches the electrode.

Figure 7:
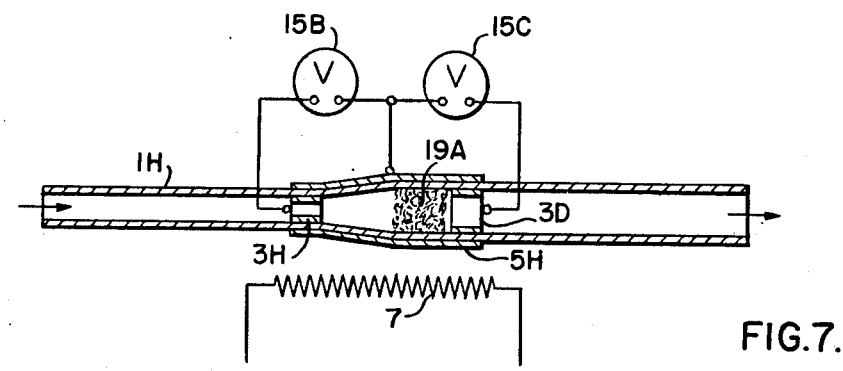

Different tube diameters may be employed for providing different flow rates or contact times. To illustrate this FIG. 7 is based on FIG. 3 but omits the plug 23 and replaces the tube 1B by a tube 1H which has a smaller cross-section to the left of the catalyst 19A. This smaller cross-section increases the flow rate of the mixture above the flow rate present in the right-hand, larger-diameter part of the tube. The electrodes 3B and 5B of FIG. 3 are replaced in FIG. 7 by corresponding electrodes 3H and 5H contoured to fit the tube 1H.

As previously pointed out the parts may be located in a single furnace. If different temperatures are desired for different parts, the parts may be located in different furnaces, or parts to be operated at a lower temperature may be spaced from the heater.

I claim:

1. An electrochemical device for monitoring constituents of an oxygen-fuel mixture comprising, a solid electrolyte electrochemical cell having a first and second electrode disposed on opposite surfaces thereof, said first electrode has a composition exhibiting negligible catalytic action on said mixture, means for supplying a first portion of said mixture to said first electrode and a second portion of said mixture to said second electrode, said first portion of said mixture forming an oxygen reference media and said first electrode serving as an oxygen reference electrode, and catalytic means for equilibrating said second portion of said mixture, said electrochemical device generating an EMF indicative of the difference between the oxygen content of said first portion of said mixture and the equilibrated second portion of said mixture.

2. An electrochemical device as claimed in claim 1 wherein said second electrode has a composition producing substantial catalytic action among the constituents of said mixture, said second electrode serving as said catalytic means.

3. An electrochemical device as claimed in claim 1 wherein said second electrode has a composition exhibiting negligible catalytic action on said mixture, and said catalytic means equilibrating said second portion of said mixture in advance of contact with said second electrode.

4. An electrochemical device as claimed in claim 3 wherein said first and second electrodes are silver compositions.

5. An electrochemical device as claimed in claim 2 wherein said first electrode is a silver composition and said second electrode is a platinum composition.

6. An electrochemical device for monitoring constituents of an oxygen-fuel mixture comprising a first solid electrolyte electrochemical cell having a first and second electrode disposed on opposite surfaces thereof, a second solid electrolyte electrochemical cell having a first and second electrode disposed on opposite surfaces thereof, means for supplying an oxygen reference media in contact with said second electrodes of said first and second solid electrolyte electrochemical devices, said second electrodes functioning as oxygen reference electrodes, means for supplying said mixture in a consecutive manner to the first electrode of said first solid electrolyte electrochemical cell device and subsequently to the first electrode of said second solid electrolyte electrochemical device, said first electrode of said first solid electrolyte electrochemical device has a composition exhibiting negligible catalytic action on said mixture, catalystic means for equilibrating said mixture following passage of said mixture in contact with said first electrode of said first solid electrolyte electrochemical device to provide an equilibrated mixture in contact with said first electrode of said second solid electrolyte electrochemical device, said first solid electrolyte electrochemical device developing an EMF between said first and second electrodes which is indicative of the actual partial pressure of oxygen in said mixture, said second solid electrolyte electrochemical device developing an EMF between said first and second electrodes which is indicative of the oxygen partial pressure of the mixture following equilibration of said mixture.

7. An electrochemical device as claimed in claim 6 wherein said first electrodes are silver compositions.

8. An electrochemical device as claimed in claim 6 wherein said first electrode of said first solid electrolyte electrochemical device is a silver composition, and said first electrode of said second solid electrolyte electrochemical device is a composition producing substantial catalytic action among the constituents of said mixture, said first electrode of said second solid electrolyte electrochemical device serving as said catalytic means.

* * * * *